(12) United States Patent
Sigvardsson et al.

(10) Patent No.: US 11,849,721 B2
(45) Date of Patent: Dec. 26, 2023

(54) METHODS OF PREPARING PH-STABILIZED AND HEAT-STERILIZED ORGAN PRESERVATION AND/OR PERFUSION SOLUTIONS

(71) Applicant: XVIVO Perfusion AB, Gothenburg (SE)

(72) Inventors: Anne-Li Sigvardsson, Gothenburg (SE); Elin Sjöqvist, Gothenburg (SE)

(73) Assignee: XVIVO PERFUSION AB, Gothenburg (SE)

( * ) Notice: Subject to any disclaimer, the term of this patent is extended or adjusted under 35 U.S.C. 154(b) by 0 days.

(21) Appl. No.: 17/655,485

(22) Filed: Mar. 18, 2022

(65) Prior Publication Data
US 2022/0202006 A1    Jun. 30, 2022

Related U.S. Application Data

(60) Continuation of application No. 16/181,659, filed on Nov. 6, 2018, now abandoned, which is a division of application No. 15/654,763, filed on Jul. 20, 2017, now abandoned, which is a continuation of application No. PCT/EP2017/050881, filed on Jan. 17, 2017.

(51) Int. Cl.
| | |
|---|---|
| *A01N 1/02* | (2006.01) |
| *A61K 31/721* | (2006.01) |
| *A61K 31/70* | (2006.01) |
| *A61M 39/08* | (2006.01) |

(52) U.S. Cl.
CPC .......... *A01N 1/0226* (2013.01); *A01N 1/021* (2013.01); *A01N 1/0221* (2013.01); *A01N 1/0247* (2013.01); *A61K 31/70* (2013.01); *A61K 31/721* (2013.01); *A61M 39/08* (2013.01); *A61M 2210/12* (2013.01)

(58) Field of Classification Search
CPC .... A01N 1/0226; A01N 1/021; A01N 1/0247; A61K 31/721
See application file for complete search history.

(56) References Cited

U.S. PATENT DOCUMENTS

| | | | |
|---|---|---|---|
| 5,552,267 A | 9/1996 | Stern et al. | |
| 5,654,266 A | 8/1997 | Chen et al. | |
| 5,945,272 A | 8/1999 | Segall et al. | |
| 6,492,103 B1 | 12/2002 | Taylor | |
| 7,255,983 B2 | 8/2007 | Steen | |
| 9,060,507 B2 | 6/2015 | Alford et al. | |
| 2014/0303254 A1* | 10/2014 | Hingorani | A61K 9/0019 |
| | | | 53/425 |

FOREIGN PATENT DOCUMENTS

| | | | |
|---|---|---|---|
| CN | 100381048 C | 4/2008 | |
| EP | 3448149 B1 | 8/2019 | |
| JP | S58192545 A | 11/1983 | |
| JP | H03223201 A | 10/1991 | |
| JP | H06506950 A | 8/1994 | |
| WO | 9218136 A1 | 10/1992 | |
| WO | 1997022244 A1 | 6/1997 | |
| WO | 2001054495 A1 | 8/2001 | |
| WO | 2002035929 A1 | 5/2002 | |
| WO | 2012072374 A1 | 6/2012 | |
| WO | 2012142487 A1 | 10/2012 | |
| WO | 2018133921 A1 | 7/2018 | |

OTHER PUBLICATIONS

Anonymous. Temperature Dependence of the PH of Pure Water; LibreTexts, p. 1 downloaded from https://chem.libretexts.org/@go/page/1293 on Apr. 10, 2023. (Year: 2023).*

Anonymous. Does Temperature Affect PH?, AtlasScientific, pp. 1-16. downloaded from: https://atlas-scientific.com/blog/does-temperature-affect ph/#:~:text=Temperature%20plays%20a%20key%20role,hydrogen%20ions%20than%20hydroxide%20ions on Apr. 10, 2023. (Year: 2023).*

Fisher, et al., "An Observational Study of Donor Ex Vivo Lung Perfusion in UK Lung Transplantation: Develop UK", Health Technology Assessment, vol. 20, No. 85 pp. 1-276 (311 pages total) (Year: 2016).

Latchana et al., Preservation Solutions for Cardiac and Pulmonary Donor Grafts: a Review of the Current Literature; Journal of Thoracic Disease, vol. 6, No. 8, pp. 1143-1149 (2014).

Saxena et al., Techniques for Lung Procurement for Transplanation Following Donation After Circulatory Death; Operative Techniques in Thoracic and Cardiovascular Surgery, vol. 19, pp. 380-393 (2014).

Bio Products Laboratory, Ltd., "Albuminex® 5% (human albumin) solution for injection," pp. 1-11, Jun. 19, 2018, available at: https://www.fda.gov/media/113691/download; last accessed Nov. 16, 2019.

(Continued)

*Primary Examiner* — Jeanette M Lieb
*Assistant Examiner* — Paul C Martin
(74) *Attorney, Agent, or Firm* — Pearne & Gordon LLP

(57) ABSTRACT

An organ preservation and/or perfusion solution for an isolated tissue or organ is provided. The solution comprises dextran, glucose, calcium ions, a buffer, and water, has a pH of 6.6 to 7.8, and is sterile based on having been subjected to heat sterilization. A method of preparing the solution also is provided. The method comprises combining dextran, glucose, calcium ions, buffer, and water to obtain an initial solution, adjusting the pH of the initial solution to 7.0 to 7.8 if needed, and subjecting the initial solution to heat sterilization, thereby obtaining the organ preservation and/or perfusion solution. A method of preserving and/or perfusing an isolated tissue or organ also is provided. A method for flushing, storage, and/or transportation of an isolated lung after removal from a donor in preparation for eventual transplantation into a recipient also is provided.

15 Claims, No Drawings

(56) References Cited

OTHER PUBLICATIONS

Pistolesi, "F0 A technical note", Fedegari Group, Jun. 27, 2014, pp. 1-34, available at: https://www.pharmaguideline.com/2011/03/d-value-z-value-and-f0-value.html, last accessed Nov. 16, 2019.
Das, et al., "Temperature Induced Morphological Transitions from Native to Unfolded Aggregated States of Human Serum Albumin", The Journal of Physical Chemistry B, vol. 118, pp. 7267-7276, Jun. 10, 2014.
MacKay, et al., "The Stabilization of Purified Human Albumin to Heat", Biochemical Journal, vol. 65, pp. 284-288, Jun. 25, 1957.
Nandlall, et al., "Real-time optical measurement of biologically relevant thernal damage in tissue-mimicking hydrogels containing bovine serum albumin", International Journal of Hyperthermia, vol. 26:5, pp. 456-464, Aug. 2010.
Neely, et al., "Survival after suspension of Perfusion During Asanguineous Cardiopulmonary Bypass," The Annals of Thoracic Surgery, vol. 5, No. 3, pp. 222-227 (1968).
Anonymous, "Blood pH: Definition of Blood pH," downloaded from https://medical-dictionary.thefreedictionary.com/blood+pH on Dec. 3, 2019 (2019).
American Chemical Society, "Teacher Guide: Lesson 3, Forming a precipitate", Chemistry: Investigating Your World, pp. 1-6, 2017, available at https://acswebcontent.acs.org/iyckit/pdf/Lesson3_TeacherGuide.pdf, last accessed Jan. 9, 2020.
Bartosova, et al., "Biocompatible Peritoneal Dialysis: The Target Is Still Way Off", Frontiers in Physiology, vol. 9, Article 1853, pp. 1-13, Jan. 7, 2019.
Buxton, et al., "Degradation of Glucose in the Presence of Electrolytes During Heat Sterilisation", Eur. J. Pharm. Biopharm., vol. 40, No. 3, pp. 172-175, 1994.
Haybrard, et al., "Factors Generating Glucose Degradation Products in Sterile Glucose Solutions for Infusion: Statistical Relevance Determination of Their Impacts", Scientific Reports, vol. 7: 11932, pp. 1-9, Sep. 20, 2017.
Krishnan, et al., "Glucose degradation products (GDP's) and peritoneal changes in patients on chronic peritoneal dialysis: Will new dialysis solutions prevent these changes?", International Urology and Nephrology, pp. 409-418, 2005.
Budavari, et al., "The Merck Index, an Encyclodedia of Chemicals, Drugs and Biologicals, Twelfth Edition", Merck Research Laboratories Division of Merck & Co., Inc., "1697. Calcium Carbonate," pp. 271-272, "5696. Magnesium Carbonate Hydroxide," p. 969, "8726. Sodium Bicarbonate," pp. 1471-1472, 1996.
Schmitt, et al., "Solutions for peritoneal dialysis in children: recommendations by the European Pediatric Dialysis Working Group" Pediatr. Nephrol., vol. 26, pp. 1137-1147, Mar. 31, 2011.
Woo, et al., "Characteristics of the Thermal Degradation of Glucose and Maltose Solutions", Prev. Nutr. Food Sci., vol. 20, No. 2, pp. 102-109, Jun. 30, 2015.
Steen, et al., "Safe Lung Perfusion for Twenty-Four Hours with Perfadex," Annals of Thoracic Surgery, vol. 57, pp. 450-457 (1994).
European Pharmacopoeia, Ninth Edition, 2016, vol. 1, Sections 5.1.1, 5.1.2, Council of Europe, pp. title page, copyright page, pp. 575-577 (cited as D23 in Opposition).
XVIVO 2019 Annual Report, 2019, pp. 1, 2, and 28 (extract and English translation) (cited as D24 in Opposition).
RedEye Equity Research, "XVIVO Perfusion", 2020, pp. 1, 2, and 49 (extract) (cited as D25 in Opposition).
UK National Health Service, "National Standards for Organ Retrieval from Deceased Donors," Oct. 15, 2018, pp. 1-6, 45-47 (extracts) (cited as D26 in Opposition).
Munshi et al., "Donor management and lung preservation for lung transplantation," Lancet Respir Med, Jun. 2013, vol. 1, pp. 318-328 (cited as D27 in Opposition).
EudraLex: The Rules Governing Medicinal Products in the European Union, vol. 4, EU Guidelines to Good Manufacturing Practice, Medicinal Products for Human and Veterinary Use, Annex 1, Manufacture of Sterile Medicinal Products, Nov. 25, 2008, pp. 1-16 (cited as D29 in Opposition).
European Medicines Agency, Guideline on the sterilisation of the medicinal product, active substance, excipient and primary container, pp. 1-15 (cited as D30 in Opposition).
European Agency for the Evaluation of Medicinal Products, Committee for Proprietary Medicinal Products, Decision Trees for the Selection of Sterilisation Methods; 2000, pp. title page and pp. 1-3 (cited as D31 in Opposition).
US Food & Drug Administration, Re: K211314 OCS Lung Solution; Jul. 29, 2021, pp. 1-7 (cited as D32 in Opposition).
Weinstein et al., "Principles of Parenteral Administration," Chapter 9 within Plumer's Principles & Practice of Infusion Therapy, Ninth Edition, editors Sharon M. Weinstein and Mary E. Hagle, published in 2014, pp. i-xviii and 173-202; (cited as D35 in Opposition).
Martis, "The impact of sterilization methods of the quality of peritoneal dialysis solutions," Chapter 24 in Quality Assurance in Dialysis, Second Edition, editors L.W. Henderson and R.S. Thuma, published in 1999, pp. cover and pp. i-vi and 267-273 (cited as D36 in Opposition).
Copeland, et al., "Donor heart and lung procurement: A consensus statement", The Journal of Heart and Lung Transplantation, vol. 39, No. 6, Jun. 2020, pp. 501-517.
U.S. Food and Drug Administration, "Compliance Program Guidance Manual, Program-7356 002A, " pp. 1-38 and attachment A pp. 1-16 (Sep. 11, 2015).
International Standards Institute (Svensk Standard ss_en iso 13408-1:2011), "Aseptic Processing of Health Care Products—Part 1: General Requirements (ISO 13408-1:2008)," Swedish Standard Institute, title pp. 1-2, initial pp. i-vii, pp. 1-56 (2011).
FDA, "Recognized Consensus Standards," available at https://www.accessdata.fda.gov/scripts/cdrh/cfdocs/cfStandards/detail.cfm?standard_identification_no=37004, pp. 1-3 (Jan. 1, 2014).
Global Transplant Solutions, "Servator P," available at http://globaltransplantsolutions.ca/gts-products-all/servator-p/, pp. 1-4 (2020).
Transmedics, Inc., "TransMedics(R) Organ Care System(TM) Clinical User Guide: OCS (TM) Lung System," available at https://www.accessdata.fda.gov/cdrh_docs/pdf16/P160013c.pdf, pp. 1-236 (2018).
Carnamedica, "LungProtect (1000 ml/2000 ml)," available at https://carnamedica.com/lungprotect/, pp. 1-3 (2020).
Hospira, "10% LMD in 5% Dextrose Injection," pp. 1-7, (revised Oct. 2018).
Meda AB, "Plasmodex solution for infusion," pp. 1-6 (including Google translation of sections 1-3 and 6) (May 12, 2006).
Oresund Pharma APS, "Rescue Flow infusion solution," pp. 1-5 (including Google translation of sections 1-3 and 6) (Jun. 12, 2020).
Meda AB, "Rheomacrodex 100 mg/ml with sodium chloride, solution for infusion," pp. 1-7 (including Google translation of sections 1-3 and 6) (Apr. 29, 2016).
Meda AB, "Macrodex 60 mg/ml with sodium chloride, solution for infusion," pp. 1-7 (including Google translation of sections 1-3 and 6) (May 12, 2016).
Sigma, "Dextran," pp. 1-3, available at https://www.sigmaaldrich.com/technical-documents/protocols/biology/dextran.html, last accessed Sep. 29, 2020 (2020).
VWR, "Dextran, M.W. 35,000-50,000, Powder," pp. 1-5, available at https://us.vwr.com/store/product/14511764/dextran-m-w-35-000-50-000-powder, last accessed Sep. 29, 2020 (2020).
XVIVO Perfusion AB, "XVIVO Perfusion launches Perfadex Plus, an upgraded ready to use version of Perfadex," pp. 1-2, https://news.cision.com/xvivo-perfusion/r/xvivo-perfusion-launches-perfadex-plus--an-upgraded-ready-to-use-version-of-perfadex,c2540365 (2018).
XVIVO Perfusion AB, "Perfadex Plus: The Gold Standard in Lung Preservation Made Ready to Use," pp. 1-3, available at https://www.xvivoperfusion.com/wp-content/uploads/2017/12/PERFADEX-PLUS-w-Click-web.pdf, last accessed Oct. 1, 2020 (2020).
Fass-Vardpersonal, "Addex-THAM," available at https://www.fass.se/LIF/product?userType=0&nplId=19660516000024, last accessed Oct. 1, 2020, pp. 1-4 (including partial Google translation) (2020).
Organ Recovery Systems, "SPS-1 (UW Solution) Static Preservation Solution," available at https://4fetz713plu53drexe2d10ht-wpengine.netdna-ssl.com/wp-content/uploads/2020/03/755-00001-Rev-G-SPS-1-IFU.pdf, pp. 1-14 (2020).

(56) References Cited

OTHER PUBLICATIONS

FDA, "Guidance for Industry: Sterile Drug Products Produced by Aseptic Processing—Current Good Manufacturing Practice", U.S. Department of Health and Human Services, initial pp. i-iv and pp. 1-59 (Sep. 2004).

U.S. Food & Drug Administration, "FDA Warns Of Potentially Contaminated SPS-1 Static Preservation Solution Distributed by Organ Recovery Systems, Inc.: FDA Safety Communication," available at https://www.fda.gov/medical-devices/safety-communications/fda-warns-potentially-contaminated-sps-1-static-preservation-solution-distributed-organ-recovery, pp. 1-5 (2017).

FDA, "Re: K170826—Trade/Device Name: Perfadex Plus," pp. 1-5 (2018).

Blood Center of Wisconsin, "Organ & Tissue Donation," Wisconsin Donor Network/Wisconsin Tissue Bank, pp. 1-57 (2020).

Piper, "The calcium paradox revisited: An artefact of great heuristic value", Cardiovascular Research, vol. 45, pp. 123-127 (2000).

Volberg, et al., "Changes in Membrane-Microfilament Interaction in Intercellular Adherens Junctions upon Removal of Extracellular Ca2+Ions", The Journal of Cell Biology, vol. 102, pp. 1932-1842 (May 1986).

Steen, "Reply: To the Editor", The Society of Thoracic Surgeons, vol. 64, pp. 1520-1522 (1997).

Kjellstrand, et al., "Degradation in Peritoneal Dialysis Fluids May be Avoided by Using Low pH and High Glucose Concentration", Peritoneal Diaylsis International, vol. 21, pp. 338-344 (Jul. 2001).

Kjellstrand, et al., "Temperature: The Single Most Important Factor for Degradation of Glucose Fluids During Storage", Peritoneal Dialysis International, vol. 24, No. 24, pp. 385-391 (Jul. 2004).

Wieslander, et al., "Cytotoxicity, pH, and Glucose Degradation Products in Four Different Brands of PD Fluid", Adv. Perit Dial, vol. 12, pp. 57-60, provided as pp. 1-5 (1996).

Linden, et al., "3,4-Dideoxyglucosone-3-ene (3,4-DGE): A cytotoxic glucose degradation product in fluids for peritoneal dialysis", Kidney International, vol. 62, pp. 697-703 (2002).

Woo, et al., "Characteristics of the Thermal Degradation of Glucose and Maltose Solutions", Prev. Nutr. Food Sci, vol. 20, No. 2, pp. 102-109, http://dx.doi.org/10.3746/pnf.2015.20.2.102, pISSN 2287-1098 • eISSN 2287-8602 (2015).

Cook, et al., "Hplc Studies on the Degradation Profies of Glucose 5% Solutions Subjected to Heat Sterilization in a Microprocessor-Controlled Autoclave", Journal of Clinical Pharmacy and Theraputics, vol. 14, pp. 189-195 (1989).

Cardella, et al., "A novel cell culture model for studying ischemia-reperfusion injury in lung transplanatation", J. Appl. Physiol., vol. 89, pp. 1553-1560 (2000).

Vitrolife AB, "Årsredovisning 2002 (Annual Report 2002) Vitrolife AB (publ)," available at https://mb.cision.com/wpyfs/00/00/00/00/00/03/5D/BD/wkr0001.pdf, pp. 1-45 (including Google translation of section "Försäljning och marknad") (2003).

XVIVO Perfusion AB, "Årsredovisning 2013 (Annual Report 2013) XVIVO Perfusion AB (Publ)," available at https://mb.cision.com/Main/4567/9564644/229847.pdf, pp. 1-41 (including Google translation of section "Perfadex(R)") (2014).

Notice of Opposition filed in European Application No. 17700817.4 (EP3448149B1), dated Jun. 18, 2020, pp. 1-38.

Rega, et al., Long-term Preservation with Interim Evaluation of Lungs from a Non-Heart-Beating Donor After a Warm Ischemic Interval of 90 Minutes, Annals of Surgery, vol. 238, No. 6, pp. 782-793 (2003) (D3 in Opposition).

Becker, et al., "Evaluating acellular versus cellular perfusate composition during prolonged ex vivo lung perfusion after initial cold ischaemia for 24 hours," Transplant International, vol. 29, pp. 88-97 (2016) (cited as D4 in Opposition).

Wallinder, et al., "Transplantation of initially rejected donor lungs after ex vivo lung perfusion," The Journal of Thoracic and Cardiovascular Surgery, vol. 144, No. 5, pp. 1222-1228 (2012) (cited as D5 in Opposition).

Pego-Fernandes, et al., "Ex vivo lung perfusion: initial Brazilian experience," Jornal Brasileiro de Pneumologia, vol. 35, No. 11, pp. 1107-1112 (2009) (note that p. 1112 is blank) (cited as D6 in Opposition).

FDA, "Perfadex FDA Premarket approval 510k" (extracts), pp. 1-61 (2014) (cited as D7 in Opposition).

Andreasson, et al, "Ex vivo lung perfusion in clinical lung transplantation: State of the art," European Journal of Cardio-Thoracic Surgery, vol. 46, pp. 779-788 (2014) (cited as D8 in Opposition).

Steen, et al., "Transplantation of Lungs from Non-Heart-Beating Donors After Functional Assessment Ex Vivo," Annals of Thoracic Surgery, vol. 76, pp. 244-252 (2003) (cited as D9 in Opposition).

NHS Cardiothoracic Advisory Group (CTAG), pp. 1-2, "Perfadex Guidelines," (2016) (cited as D10 in Opposition).

European Medicines Agency, "Consultation procedure Public Assessment Report—Medical Device: Steen solution," pp. 1-20 (2012) (cited as D12 in Opposition).

Loor et al., "Prolonged EVLP Using OCS Lung: Cellular and Acellular Perfusates," Transplantation, vol. 101, No. 10, pp. 2303-2311 (Oct. 2017), available at https://www.ncbi.nlm.nih.gov/pmc/articles/PMC5481503/, provided as author manuscript from PMC, pp. 1-20 (cited as D13 in Opposition).

Merck Index Online, "Tromethamine," pp. 1-2 (last revised 2013) (cited as D14 in opposition).

FDA, "Premarket Notification Summary: Perfadex with THAM," pp. 1-5 (2008) (cited as D15 in opposition).

FDA, "Summary of Safety and Probable Benefit: XVIVO Perfusion System (XPS) with STEEN Solution Perfusate," pp. 1-52 (2014) (cited as D16 in opposition).

Spitzer et al., "Regulation of Intracellular pH in Mammalian Cells", Chapter 1, pp. 1-15, in The Sodium-Hydrogen Exchanger: From Molecule to its Role in Disease, ed. Morris Karmazyn et al., Springer Science +Business Media New York (2003).

Hiramatsu et al., "Influence of pH of Preservation Solution on Lung Viability", Ann. Thorac. Surg., vol. 58, pp. 1083-1086 (1994).

Shiraishi et al.., "Effects of pH and Temperature on Lung Preservation: A Study with an Isolated Rat Lung Reperfusion Model," Ann. Thorac. Surg., vol. 57, pp. 639-643 (1994).

Gillespie et al., "Adverse Effects of Tris Hydrochloride, a Commonly Used Buffer in Physiological Media," J. Physiol., vol. 259, pp. 561-573 (1976).

Altura et al., "Adverse Effects of Artificial Buffers on Contractile Responses of Arterial and Venous Smooth Muscle," Br. J. Pharmac., vol. 69, pp. 207-214 (1980).

Stinson et al., "An Evaluation of the Effects of Five Buffers on Respiratory Parameters of Isolated Mitochondria," Can. J. Biochem. Physiol., vol. 46, pp. 43-50 (1968), Abstract Only.

Lambotte et al., The Effect of Tris(hydroxymethyl)aminomethane on the Potassium Content and the Membrane Potential of Liver Cells, The Journal of Pharmacology and Experimental Therapeutics, vol. 176, pp. 434-440 (1971), Abstract Only.

Sakai et al., "Effect of Tris Buffer on the Contractile Responses of Rat Vas Deferens," Eur. J. Pharmacol., vol. 95, pp. 161-169 (1983), Abstract Only.

Turlapaty et al., "Influence of Tris on Contractile Responses of Isolated Rat Aorta and Portal Vein," Am. J. Physiol., vol. 235, pp. H208-213 (1978), Abstract Only.

"Clarity and Degree of Opalescence of Liquids", European Pharmacopoeia 5.0, 01/2005:20201, 2005, pp. 23-24.

Dextrans, http://www.sigmaaldrich.com/life-science/biochemicals/biochemical-products.html?TableP, Sigma-Aldrich Co. LLC, (downloaded Jan. 8, 2017) pp. 1-4.

"Directive 2010/45/EU of the European Parliament and of the Council of Jul. 7, 2010 on the framework for the standards of quality and safety of human organs intended for transplantation," Official Journal of the European Union L 207, vol. 53, Aug. 6, 2010, cover page and pp. 14-28.

Ingemansson, R, et al., "Importance of Calcium in Long-Term Preservation of the Vasculature", The Annals of Thoracic Surgery, the Soceity of Thoracic Surgeons, vol. 61, 1996, pp. 1158-1162.

Fisher, B., U.S. Food and Drug Administration, "Letter Regarding Low Potassium Dextran Solution with Tris Diluent", Mar. 7, 2016, pp. 1-5.

(56) References Cited

OTHER PUBLICATIONS

Ledebo, I., et al., "Can We Prevent the Degradation of Glucose in Peritoneal Dialysis Solutions?", International Society for Peritoneal Dialysis, Peritoneal Dialysis International, vol. 20, Suppl. 2, 2000, pp. S-48 to S-51.

Mikami, Y., et al., "Effects of Sugar and Buffer Types, and pH on Formation of Maillard Pigments in the Lysine Model System", Food Science and Technology Research, Japanese Society for Food Science and Technology, vol. 21, 2015, pp. 813-819.

Nilsson Thorell, C., et al., "Heat Sterilization of Fluids for Peritoneal Dialysis Gives Rise to Aldehydes", Peritoneal Dialysis International, vol. 13, 1993, pp. 208-213.

PCT/EP2017/050881, "Notification of Transmittal of International Search Report and the Written Opinion of the International Searching Authority, or the Declaration", dated Mar. 7, 2017.

PCT/EP2017/050881, Specification and Filing Receipt, filed Jan. 17, 2017.

Wieslander, A., et al., "Heat Sterilization of Glucose-Containing Fluids for Peritoneal Dialysis: Biological Consequences of Chemical Alterations", Biocompatibility of Peritoneal Dialysis Solutions, Peritoneal Dialysis International, International Society for Peritoneal Dialysis, vol. 15, No. 7 (Suppl.), 1995, pp. 1-9.

Borzova, et al., "Kinetics of Thermal Denaturation and Aggregation of Bovine Serum Albumin", 2016, PLoS ONE 11 (4): e0153495. doi:10.1371/journal.pone.0153495, pp. 1-29.

Genetic Science Learning Center, Sterilizing Liquids, 2015, University of Utah, pp. 1-2, available at http://teach.genetics.utah.edu/content/microbiology/liquids/ (last accessed Jan. 8, 2018).

Gibraltar Laboratories, "Difference between Moist Heat Sterilization & Dry Heat Sterilization", 2017, pp. 1-9, available at https://gibraltarlabsinc.com/difference-between-moist-heat-sterilization-dry-heat-sterilization/ (last accessed Jan. 5, 2018).

Maathuis, et al., "Perspectives in Organ Preservation", Transplantation, vol. 83, No. 10, 2007, pp. 1289-1298.

Trocha, et al., "Organ Preservation Solutions Increase Endothelial Permeability and Promote Loss of Junctional Proteins", Annals of Surgery, vol. 230, No. 1, 1999, pp. 105-113.

Hauet, et al, "A new approach in organ preservation: potential role of new polymers", Kidney International, vol. 74, 2008, pp. 998-1003.

Porteous, et al., "Primary graft dysfunction: lessons learned about the first 72 hours after lung transplantation, Curr Opin Organ Transplant.", vol. 20, No. 5, 2015, pp. 506-514, available in PMC Oct. 1, 2016, doi:10.1097/MOT.0000000000000232, pp. 1-22.

Christie, et al., "Report of the ISHLT Working Group on Primary Lung Graft Dysfunction Part II: Definition. A Consensus Statement of the International Society for Heart and Lung Transplantation", The Journal of Heart and Lung Transplantation, vol. 24, No. 10, 2004, pp. 1454-1459.

Cardioplegia Solution A, "Solution for cardiac perfusion in viaflex plastic container", New Zealand Data Sheet, Baxter Healthcare Ltd, Mar. 30, 2016, pp. 1-5.

* cited by examiner

METHODS OF PREPARING PH-STABILIZED AND HEAT-STERILIZED ORGAN PRESERVATION AND/OR PERFUSION SOLUTIONS

CROSS-REFERENCE TO RELATED APPLICATIONS

This application is a continuation of U.S. application Ser. No. 16/181,659, filed Nov. 6, 2018, now abandoned, which is a divisional of U.S. application Ser. No. 15/654,763, filed Jul. 20, 2017, now abandoned, which is a continuation of International Application No. PCT/EP2017/050881, filed Jan. 17, 2017, all of which are incorporated herein by reference.

FIELD OF INVENTION

The present invention relates to organ preservation and/or perfusion solutions for an isolated tissue or organ, the solutions comprising dextran, glucose, calcium ions, a buffer, and water, having a pH of 6.6 to 7.8, and being sterile based on having been subjected to heat sterilization, as well as methods of making and using such solutions.

BACKGROUND TO THE INVENTION

Dextran solutions have been used for different medical purposes for more than 50 years. Perfadex® solution is a heat-sterilized dextran solution that was developed for organ perfusion in the early 1970s. Over the last fifteen to twenty years it has become the predominant product for preservation of lungs before transplantation. Macrodex® solution and Rheomacrodex® solution have been used for even longer as plasma expanders during surgery and in trauma patients. PrimECC® (PCT/EP2011/069524) solution is another dextran solution indicated as a priming solution for extracorporeal circulation machines. All of these solutions are provided commercially with a sub-physiological pH of about 4 to 6. The solutions might be slightly buffered with phosphate and/or bicarbonate, but as the pH decreases during heat sterilization due to hydrolysis of dextran, the pH in the product as provided commercially is below 6.6, and often below 6 at the temperature of its use. This sub-physiological pH has not been a main concern for products being infused, such as Macrodex® solution or PrimECC® solution, as the acidity is weak, and the plasma contents, mainly serum albumin, instantly buffer to maintain physiological pH in the plasma.

When a dextran solution is used to flush or perfuse an isolated organ, there is not as much plasma components such as serum albumin left and the buffering capacity is therefore reduced in the isolated organ or tissue. Thus, in practice users generally buffer Perfadex® solution with tris(hydroxymethyl)aminomethane (hereinafter TRIS, also termed THAM) or similar buffers to reach physiological pH just prior to use. The buffering of Perfadex® solution by users (also termed pre-use buffering) has been accepted, but there is always a risk to make mistakes when a product is not provided ready-to-use. The user might forget altogether to buffer the solution, or the user might use the wrong buffer or the wrong concentration. Any of these circumstances might negatively affect the quality of the isolated organ, for example lung or lungs. Therefore, a ready-to-use pre-buffered organ perfusion solution would improve organ preservation safety as well as user convenience.

WO2012/142487 describes a lung perfusion solution called OCS Solution, comprising Dextran 40, magnesium, potassium, sodium, nutrients such as glucose, hormones, buffer etc. The reference teaches that pH of the OCS Solution is monitored during production, that the OCS Solution is heat sterilized, that the OCS Solution is supplemented with a cellular medium prior to use, and that the pH of the resulting medium is adjusted prior to use with, for example, bicarbonate (paragraphs [0010], [0035], [0045], and [0066]), indicating that the OCS Solution is provided at a sub-physiological pH, which requires further buffering prior to use.

Non-autoclaved sterile filtered dextran solutions, such as STEEN Solution (PCT/SE01/02419), have been used at physiological pH for about 15 years, but to the knowledge of the present inventors no heat-sterilized dextran solutions with a pH of between 6.6 and 7.8 for medical use, has been available. Sterile filtration is acceptable for low volume products, generally with low dextran content. Otherwise dextran would clog the filter.

Another problem with heat sterilization of solutions that comprise glucose in particular, especially solutions for peritoneal dialysis, is degradation of glucose to toxic degradation products. Attempts have been made to reduce those toxic by-products, through further lowering the pH in the solution to around 3, during heat sterilization, or through separation of electrolytes and glucose during sterilization (Ledebo et al., 2000, and Wieslander et al., 1995).

The same problem of glucose degradation is known from production of dextran solutions for various medical purposes such as organ preservation. The main answer to this problem has been to increase the amount of glucose in the solution prior to sterilization to ensure sufficient glucose in the final product for use to support the organ metabolism. This answer does not consider any potential toxic effect of the glucose degradation products. If anything, the overload of glucose during production makes the problem worse through generation of increased amounts of potentially toxic glucose degradation products.

SUMMARY OF THE INVENTION

The present invention provides an organ preservation and/or perfusion solution for an isolated tissue or organ that addresses these problems and provides additional advantages. The solution comprises dextran, glucose, calcium ions, a buffer, and water. The solution has a pH of 6.6 to 7.8 and is sterile based on having been subjected to heat sterilization. The isolated tissue or organ can be selected, for example, from among lung, heart, liver, kidney, pancreas, and/or intestine. The solution is buffered at a physiologically acceptable pH for the temperature of its use prior to heat sterilization (also termed pre-buffering), and is supplemented with calcium ions to mimic extracellular fluid also prior to heat sterilization (also termed pre-calcium supplementation), and then is subjected to heat sterilization. Hence, the resulting solution is ready-to-use, as it does not require any further buffering, or any further supplementation, with calcium or any other compounds, prior to use. Moreover, the combination of pre-buffering and pre-calcium supplementation prior to heat sterilization provides protection for the glucose during heat sterilization, maintaining a higher glucose concentration in the solution and thereby reducing the production of potentially toxic degradation products.

The present invention also provides a method of preparing the organ preservation and/or perfusion solution for an isolated tissue or organ. The method comprises a step of (1) combining the dextran, the glucose, the calcium ions, the buffer, and the water to obtain an initial solution. The method also comprises a step of (2) adjusting the pH of the initial solution to 7.0 to 7.8 if needed. The method also comprises a step of (3) subjecting the initial solution to heat sterilization, thereby obtaining the organ preservation and/or perfusion solution.

The present invention also provides a method of preserving and/or perfusing an isolated tissue or organ. The method comprises a step of (1) obtaining a volume of the organ preservation and/or perfusion solution for an isolated tissue or organ from a sterile container in which the solution has been stored. The method also comprises a step of (2) administering the obtained volume of the solution to the isolated tissue or organ, thereby preserving and/or perfusing the isolated tissue or organ.

The present invention also provides a method for flushing, storage, and/or transportation of an isolated lung after removal from a donor in preparation for eventual transplantation into a recipient. The method comprises a step of (1) flushing the isolated lung of the donor with a flushing volume of an organ preservation and/or perfusion solution for an isolated tissue or organ. The method also comprises a step of (2) filling a sterile organ storage container at least partially with a filling volume of the solution and immersing the isolated lung in the filling volume of the solution.

DESCRIPTION

Organ Preservation and/or Perfusion Solutions

As noted above, the present invention provides an organ preservation and/or perfusion solution for an isolated tissue or organ. The solution comprises dextran, glucose, calcium ions, a buffer, and water. The solution has a pH of 6.6 to 7.8 and is sterile based on having been subjected to heat sterilization.

Solutions containing dextran, e.g. Dextran 40, and low levels of potassium, e.g. extracellular levels, have been used for organ preservation since the 1960s, with the solutions variously being termed, for example, dextran solutions, Dextran 40 solutions, and/or LPD solutions.

In the late 1990s an LPD solution named Perfadex® solution became the predominant preservation solution for use with endothelium-rich organs such as lungs. The composition of Perfadex® solution (provided as mass/L) is as follows:

| | |
|---|---|
| Dextran-40 | 50 g |
| Sodium Chloride | 8 g |
| D-Glucose monohydrate | 1 g |
| Potassium Chloride | 400 mg |
| Magnesium sulphate 7H2O | 200 mg |
| Disodium phosphate 12H2O | 117 mg |
| Potassium dihydrogen phosphate | 63 mg |

Alternative electrolyte compositions can be used, as long as they are physiologically acceptable and have an electrolyte composition relatively close to that of plasma.

Dextrans

As noted, the organ preservation and/or perfusion solution as disclosed herein comprises dextran. Dextrans are polysaccharides with molecular weights of greater than or equal to 1000 daltons (Da), which have a linear backbone of α-linked D-glucopyranosyl repeating units, and which can be grouped into three classes, Class 1, Class 2, and Class 3, based on their structures. Dextrans that are commercially available may be classified according to source and/or weight average molecular weight. Commercially available dextrans include, for example, dextrans obtained from *Leuconostoc* spp. or *Leuconostoc mesenteroides*. Commercially available dextrans also include, for example, dextrans having weight average molecular weights of approximately 20000 Da, also termed Dextran 20, approximately 40000 Da, also termed Dextran 40, approximately 60000 Da, also termed Dextran 60, and approximately 70000 Da, also termed Dextran 70, among others, as well as mixtures of these dextrans, and of others.

Dextran 40 is ideal for organ preservation, due to the optimal molecular size, which provides sufficient oncotic pressure in dextran solutions without increasing the viscosity unnecessarily, particularly when provided at 40 to 60 g/L, preferably 50 g/L, in dextran solutions. However, Dextran 60, Dextran 70, or any other Dextran having an oncotic molecular size distribution between those of Dextran 20 and Dextran 70 might replace Dextran 40 to provide acceptable outcomes.

Accordingly, in some embodiments of the organ preservation and/or perfusion solution as disclosed herein, the dextran has a weight average molecular weight of 20000 to 70000 Da, for example 30000 to 50000 Da, or 33000 to 42000 Da. Also in some embodiments, the dextran comprises Dextran 40. Also in some embodiments, the dextran is present in the solution at a concentration of 40 to 60 g/L, for example 45 to 55 g/L, 48 to 52 g/L, or 50 g/L. Also in some examples, the dextran comprises a dextran obtained from *Leuconostoc* spp. or *Leuconostoc mesenteroides*.

Glucose, Calcium Ions, and Buffer

As noted, the organ preservation and/or perfusion solution as disclosed herein also comprises glucose and calcium ions.

For the last 15 years or so, Perfadex® solution has been used on about 90% of all lung grafts prior to transplantation. Perfadex® solution, like all other commercial Dextran 40 solutions, has been provided commercially at a low pH of about 4 to 6 and has therefore required buffering, to obtain a higher pH, just prior to use. This buffering has predominantly been done with TRIS. The reason why Perfadex® solution has been provided at a low pH is to increase the stability of the product, particularly glucose therein, not the least during heat sterilization. As discussed in detail below, the present inventors have shown that, contrary to the prior art, in the organ preservation and/or perfusion solution as disclosed herein an increased pH of 7.0 to 7.8, preferably 7.4±0.2, prior to heat sterilization stabilizes glucose during the heat sterilization process.

Many users have also supplemented Perfadex® solution with a sterile solution of calcium ions just prior to use, as this has been shown to be beneficial for the endothelium (Ingemansson et al., 1996). One reason why calcium ions were not included in the Perfadex® solution until just prior to use was that there was an expectation that if the calcium ions were added prior to heat sterilization of the Perfadex® solution, then calcium phosphate would precipitate during heat sterilization and subsequent storage. Surprisingly, the present inventors have shown that the organ preservation and/or perfusion solution as disclosed herein does not exhibit formation of precipitate during heat sterilization or subsequent storage for 24 months following the heat sterilization. Moreover, contrary to the prior art, the inventors have shown that supplementation of calcium ions, together with a pH of 7.0 to 7.8, preferably 7.4±0.2, synergistically stabilizes glucose during heat sterilization.

For these reasons both TRIS buffering and calcium ion supplementation of Perfadex® solution were understood to be beneficial or even necessary for ultimate use, but neither TRIS nor calcium ions were previously provided in the Perfadex® solution until just prior to use due to the expected problems during heat sterilization and storage. One advantage of the organ preservation and/or perfusion solution as disclosed herein, based on pre-buffering and pre-calcium supplementation prior to heat sterilization, is that the organ preservation and/or perfusion solution can be provided as a ready-to-use product. A ready-to-use product provides convenience for the user and improves safety, as there is less risk involved, in terms of faulty buffering and/or other supplementation, when no further buffering or other supplementation is required.

Accordingly, in some embodiments of the organ preservation and/or perfusion solution as disclosed herein, the glucose was present in the solution at 0.5 to 5 g/L before the heat sterilization, e.g. at 0.6 to 3 g/L, 0.8 to 2 g/L, 0.9 to 1.5 g/L, or 1 g/L. By this it is meant that the glucose was present in an initial solution at 0.5 to 5 g/L, prior to subjecting the initial solution to heat sterilization to obtain the organ preservation and/or perfusion solution, and thus prior to partial degradation of glucose that occurs during the heat sterilization. Thus, in some examples, the glucose can be added to an initial solution at 0.5 to 5 g/L, and then the initial solution can be subjected to heat sterilization, thereby providing the organ preservation and/or perfusion solution in which the glucose was present in the solution at 0.5 to 5 g/L.

Also in some embodiments, glucose degradation during heat sterilization was less than 10%, e.g. less than 9.5%, or less than 9.0%. By this it is meant that heat sterilization of an initial solution, to obtain the organ preservation and/or perfusion solution, results in the organ preservation and/or perfusion solution having a concentration of glucose that is lower than the concentration of glucose that was present in the initial solution, the decrease again being due to partial degradation of glucose that occurs during the heat sterilization, and the decrease being less than 10% of the concentration of glucose that was present in the initial solution.

Also, in some embodiments of the organ preservation and/or perfusion solution as disclosed herein, the calcium ions are present in the solution at a concentration of 0.3 to 1.5 mM, e.g. 0.4 to 1 mM, or 0.5 mM. Also in some embodiments, the solution does not result in precipitate during 24 months of storage at 5 to 25° C. Also in some embodiments, the solution further comprises phosphate ions. Also in some embodiments, the phosphate ions are present in the solution at a concentration of 0.2 to 0.8 mM, e.g. 0.7 to 0.8 mM.

Solution Temperature, Buffer Choice, and pH

As noted, the organ preservation and/or perfusion solution as disclosed herein also comprises a buffer. Moreover, the solution has a pH of 6.6 to 7.8 and is sterile based on having been subjected to heat sterilization.

Organ flush perfusion and preservation is done at sub-physiological temperatures. Normally a room-temperature flush is done at the start of organ flushing, then cold flush and cold preservation are done at 2 to 15° C. The pH of the corresponding dextran solution is dependent on the temperature. This is especially true when a buffer such as TRIS is used in the dextran solution. The pH of a TRIS buffered solution increases about 0.01 pH units per degree Celsius decrease. Conventionally, pH is measured at room temperature, meaning 18 to 25° C., or more particularly 25° C. The temperature difference in going from 25° C. to 5° C. results in a pH increase of about 0.2 pH units for a TRIS buffered solution.

Tissues, especially lungs, are more sensitive to pH above 7.4, and particularly above 7.8, than to pH below 7.4. Therefore it is beneficial if the pH in the dextran solution is not above 7.8 at any temperature of its use, and preferably is not above 7.6. On the lower range, a pH as low as 6.6, measured at 25° C., would be acceptable for storage at 2 to 15° C., since the pH of the dextran solution would be somewhat higher at the lower temperature. The lung tissue would also sustain the short period of flushing at room temperature with a solution with a pH as low as 6.6, especially as there is more serum albumin present in the vasculature during flushing than during preservation, and as the serum albumin will buffer the weak acidity of the dextran solution.

As noted, the organ preservation and/or perfusion solution as disclosed herein can be pre-buffered with TRIS. Pre-buffering with TRIS utilizes the temperature dependency of the TRIS buffer and thereby maintains an acceptable pH post heat sterilization for its intended temperature of use, and no buffering is required by the user. The pH of solution before heat sterilization, i.e. the pH of an initial solution that will be heat sterilized to yield the organ preservation and/or perfusion solution, should preferably be 7.0 to 7.8, at room temperature, or 25° C., before the heat sterilization, more preferably 7.2 to 7.6. The pH of the solution generally will have decreased by up to 0.4 pH units, and more particularly 0.1 to 0.3 pH units, following heat sterilization due to glucose and dextran degradation. Accordingly, by preparing an initial solution with a pH of 7.0 to 7.8, at room temperature, or 25° C., more preferably 7.2 to 7.6, before heat sterilization, the organ preservation and/or perfusion solution will have a pH suitable for organ preservation and/or perfusion following heat sterilization, e.g. a pH of 6.6 to 7.8, a pH of 6.7 to 7.7, or a pH of 6.9 to 7.6, also at room temperature, or 25° C.

As will be appreciated, the organ preservation and/or perfusion solution as disclosed herein also can be pre-buffered with buffers other than, or in addition to, TRIS, e.g. an organic or biological buffer other than, or in addition to, TRIS, based on similar principles as discussed for TRIS. An example of such an alternative buffer is BIS-TRIS.

As will also be appreciated, the organ preservation and/or perfusion solution as disclosed herein can be heat sterilized based on steam sterilization in an autoclave at a suitable temperature for a suitable time, e.g. at 121° C. for 20 minutes or more or with alternative time and temperature to reach F0 of 12-15.

Accordingly, in some embodiments of the organ preservation and/or perfusion solution as disclosed herein, the buffer comprises an organic or biological buffer that is present in the solution at a concentration of 1 to 15 mM, e.g. 1.5 to 10 mM, 2 to 5 mM, or 3 mM. Also in some examples, the organic or biological buffer comprises TRIS at a concentration of 1 to 5 mM, e.g. 1.5 to 4 mM, or 3 mM.

Also, in some embodiments the organ preservation and/or perfusion solution has a pH of 6.6 to 7.8 at room temperature, e.g. at 18 to 25° C., or at 25° C. Also in some embodiments the solution has a pH of 6.7 to 7.7, or a pH of 6.9 to 7.6, also at room temperature, e.g. at 18 to 25° C., or at 25° C.

Also, in some embodiments the organ preservation and/or perfusion solution is sterile based on having been subjected to heat sterilization based on steam sterilization in an autoclave, e.g. at 115 to 130° C., or at 118 to 123° C., or at 121° C., for at least 5 minutes, or at least 10 minutes, or for 20 minutes or more, to achieve an F0 of at least 10, or at least 12, or at least 15, or of 12 to 15.

Glucose Degradation During Heat Sterilization

Considering glucose degradation in more detail, glucose degradation during heat sterilization has mainly been investigated in relation to peritoneal nutrition solutions and in solutions for peritoneal dialysis. These solutions contain relatively high concentrations of glucose, typically about 1.5%, and are often used repeatedly on the same patient. The subject of glucose degradation in peritoneal dialysis solutions, its toxic effects, and preventive measures taken to avoid the toxic effects, have been thoroughly investigated by researchers at the University Hospital of Lund together with the researchers at Gambro AB, in Lund Sweden. Their results have been published in a number of publications, some of which are referenced here as (Nilsson Thorell et al., 1993, Ledebo et al., 2000, and Wieslander et al., 1995). In (Nilsson Thorell et al., 1993) a number of glucose degradation products were identified as acetaldehyde, 5-HMF, glyoxal, methylglyoxal, formaldehyde, and 2-furaldehyde. It was also concluded that there were more unidentified degradation products present that might be responsible for the cytotoxic effects seen after heat sterilization of peritoneal dialysis solutions.

The answers for avoiding glucose degradation, as proposed by (Ledebo et al., 2000, and Wieslander et al., 1995), are primarily based on avoiding heat sterilization. If a solution must be heat sterilized, then this should be done at a low pH, preferentially around 3 to 3.5, or glucose should not be sterilized together with the electrolytes.

In dextran solutions for organ perfusion, the glucose concentration generally is about 0.05 to 0.5%. It has been well recognised that glucose is degraded during heat sterilization and this has been counteracted through over-supplementation of glucose during production by about 5 to 10%, to at least be closer to the estimated target in the final product following heat sterilization. Typically, 10 to 15% of the glucose would be degraded during heat sterilization based on steam sterilization as described above, e.g. to achieve an F0 of 12 to 15. The potentially toxic effects of the degradation products have not been considered, probably because the subsequent exposure is short and one-time. Although no such direct toxicity has been observed with use of dextran solutions for organ perfusion, a reduction of potentially toxic glucose degradation products, as achieved for the organ preservation and perfusion solution as disclosed herein, should be beneficial as it should further improve safety of the product. Another advantage with stabilized glucose during production of the organ preservation and/or perfusion solutions is that it better guarantees the important glucose content in the final product at levels that will support the metabolism during storage of an isolated tissue or organ.

Glucose Stabilization

Considering glucose stabilization in more detail, as is shown in the referenced prior art (Ledebo et al., 2000, and Wieslander et al., 1995), a low pH is considered essential to reduce glucose degradation and formation of glucose degradation products. Furthermore (Wieslander et al., 1995) states that $Ca^{2+}$ is a catalytic substance for the glucose degradation and suggests that $Ca^{2+}$, along with $Mg^{2+}$, $Cl^-$, and $Na^+$ ions, should be kept separated from the glucose during heat sterilization.

As noted above, the present inventors have shown that, contrary to the prior art, an increased pH of 7.0 to 7.8, preferably 7.4±0.2, prior to heat sterilization stabilizes glucose during the heat sterilization process, again based on steam sterilization as described above, e.g. to achieve an F0 of 12 to 15. Also as noted, contrary to the prior art, the present inventors have shown that supplementation of calcium ions, together with a pH of 7.0 to 7.8, preferably 7.4±0.2, synergistically stabilizes glucose during heat sterilization. No stabilizing effect is seen when the solution is supplemented with calcium ions but without the increased pH. As is shown in Table 2 of Example 1, the two solutions without pH adjustment and without a heat sterilization stable organic or biological buffer such as TRIS (i.e. LPD and LPD+CaCl2) lose almost 13% of the glucose due to degradation of the glucose during heat sterilization, whereas in the TRIS buffered solution adjusted to a pH of 7.4±0.2 (LPD+ TRIS) the degradation is less than 10%, and with also calcium ion supplementation (LPD+TRIS+CaCl2) the degradation is less than 9%.

As described above the organ preservation and/or perfusion solution as disclosed herein is pre-buffered to a physiologically acceptable pH and supplemented with a low concentration of calcium ions, which provides a more plasma-like electrolyte matrix for the solution. The buffering with TRIS to a physiologically acceptable pH has a glucose-protective effect during heat sterilization. Moreover, the combination of calcium ions and a physiologically acceptable pH of the solution synergistically further stabilizes glucose during heat sterilization.

Selection of Buffer

Considering buffers in more detail, buffers for the organ preservation and/or perfusion solution as disclosed herein, being intended for heat sterilization, must be carefully selected, as many buffers, such as MOPS and HEPES, might degrade during heat sterilization. Another important factor, when selecting a buffer for a near physiological electrolyte solution, is the risk of precipitation between the buffer and divalent cations during production and throughout the shelf-life of the product. Bicarbonate and phosphate are both known to precipitate with calcium and magnesium ions when present in concentrations above the solubility limits. TRIS is an ideal buffer for heat sterilized solutions, although other buffers providing the same two properties of being heat sterilizable and not forming precipitate with divalent cations might be used. Another beneficial factor for a buffer used in a perfusion and/or preservation solution for use at hypothermia of less than or equal to 25° C., or preferably less than or equal to 15° C., is pH dependency of temperature. As noted above, TRIS provides an increase of pH of about 0.01 per degree Celsius decrease. This means that the solution might be stored at a slightly lower pH at room temperature, providing stability to the product, without compromising the required acceptable physiological pH at the lower temperature of use.

The concentration of the buffer should be sufficient to maintain a pH of 6.6 to 7.8 throughout the product shelf-life, but should not exceed any toxicity level for the tissue. For TRIS a concentration in the final solution of 1 to 15 mM, or preferably 1 to 5 mM, is considered both sufficient and safe.

Calcium Ion Source

The calcium ion source for the organ preservation and/or perfusion solution as disclosed herein can be any soluble physiologically acceptable calcium ion salt, such as calcium lactate, calcium gluconate, or preferably calcium chloride. The concentration of calcium ions in the organ preservation and/or perfusion solution should be similar to the concentration in human plasma, which is about 1.5 mM. A slightly lower concentration could be beneficial as it reduces the risk of precipitation with phosphate ions present in the solution. The optimal concentration of calcium ions in the solution is therefore 0.3 to 1.5 mM.

Water

As noted, the organ preservation and/or perfusion solution as disclosed herein also comprises water. Suitable water includes water of extra high quality, such as water for injection.

Methods of Preparing the Organ Preservation and/or Perfusion Solutions

As noted above, the present invention also provides a method of preparing the organ preservation and/or perfusion solution for an isolated tissue or organ.

The method comprises a step of (1) combining the dextran, the glucose, the calcium ions, the buffer, and the water to obtain an initial solution. The method also comprises a step of (2) adjusting the pH of the initial solution to 7.0 to 7.8, or to 7.2 to 7.6, if needed. The method also comprises a step of (3) subjecting the initial solution to heat sterilization, thereby obtaining the organ preservation and/or perfusion solution.

Methods of Preserving and/or Perfusing an Isolated Tissue or Organ

As noted above, the present invention also provides a method of preserving and/or perfusing an isolated tissue or organ.

The method comprises a step of (1) obtaining a volume of the organ preservation and/or perfusion solution for an isolated tissue or organ from a sterile container in which the solution has been stored. The method also comprises a step of (2) administering the obtained volume of the solution to the isolated tissue or organ, thereby preserving and/or perfusing the isolated tissue or organ. The sterile container can be, for example, a sterile fluid bag, such as a 1000 mL sterile fluid bag, or a 3000 mL sterile fluid bag, among other containers.

In some embodiments of the method, the obtaining of step (1) comprises inserting sterile tubing into the sterile container and allowing the volume of the solution to flow from the sterile container through the sterile tubing, and the administering of step (2) comprises administering the obtained volume of the solution from the sterile tubing to the isolated tissue or organ.

Also in some embodiments, the administering of step (2) is carried out at hypothermia of less than or equal to 25° C. For example, in some embodiments, the administering of step (2) is carried out at hypothermia of 2 to 15° C.

Also in some embodiments, the obtained volume of the solution is not supplemented with additional ingredients during or between steps (1) and (2). In accordance with these embodiments, the obtained volume of the solution is not supplemented with additional buffer, nor acid or base, nor culture media, nor any other additional ingredients, during or between steps (1) and (2). As will be appreciated, in accordance with these embodiments the solution has been provided ready-to-use. As also will be appreciated, though, in other embodiments the obtained volume of the solution may be subjected to further supplementation with additional ingredients, depending on circumstances of the preservation and/or perfusion.

Also in some embodiments, the isolated tissue or organ comprises one or more of lung, heart, liver, kidney, pancreas, and/or intestine. The isolated tissue or organ can be either circulatory isolated within the donor body cavity, or after retrieval from the donor body, or both in sequence.

Methods for Flushing, Storage, and/or Transportation of an Isolated Lung after Removal from a Donor in Preparation for Eventual Transplantation into a Recipient As noted above, the present invention also provides a method for flushing, storage, and/or transportation of an isolated lung after removal from a donor in preparation for eventual transplantation into a recipient.

The method comprises a step of (1) flushing the isolated lung of the donor with a flushing volume of an organ preservation and/or perfusion solution for an isolated tissue or organ. The method also comprises a step of (2) filling a sterile organ storage container at least partially with a filling volume of the solution, and immersing the isolated lung in the filling volume of the solution.

In accordance with this method, the organ preservation and/or perfusion solution can serve as a pre-buffered, extracellular solution containing Dextran 40 and calcium that can be used for rapid cooling, perfusion, and storage of lungs in connection with transplantation. Administration of the solution at the recommended temperatures will effectively cool the organ to reduce its metabolic requirements. Aseptic technique should be used.

Also in accordance with this method, steps (1) and (2) can be carried out in various orders. For example, the flushing of step (1) can be carried out first, followed by the filling of step (2), then the immersing of step (2). Also for example, the filling of step (2) can be carried out first, followed by the flushing of step (1), then the immersing of step (2). Also for example, the flushing of step (1) and the filling of step (2) can be carried out at the same time, followed by the immersing of step (2).

In some embodiments of the method, the flushing of step (1) might initially be done at room temperature to more thoroughly remove blood from the circulation followed by cold flushing carried out at 2 to 8° C. The flushing should preferably be done both antegrade and retrograde. The filling according to step (2) is preferably done at 2 to 8° C. This can be done, for example, based on the flushing volume of the solution being provided first at room temperature, then at 2 to 8° C., and by the filling volume of the solution being provided at 2 to 8° C.

Also in some embodiments, the flushing of step (1) results in an effluent of the isolated lung and is carried out until the effluent is clear. For example, the flushing can be carried out by administering the flushing volume of the solution by continuous flow, resulting in an effluent of the isolated lung. Also for example, the flushing can be carried out until the effluent has a clarity that is the same as that of a reference volume of the organ preservation and/or perfusion solution that has not been used for flushing.

Also in some embodiments, the flushing volume of the solution corresponds to 50 to 75 mL of the solution per kg body weight of the donor and/or from 3 to 8 L of the solution, although in other embodiments the flushing volume may be greater or lower than these volumes.

Also in some embodiments, the method further comprises steps of (3) sealing the sterile organ storage container, with the isolated lung contained therein, with a sterile closure; and then (4) maintaining the sterile organ storage container at 2 to 8° C. for up to 12 hours, depending on the initial quality of lung, prior to transplantation of the isolated lung into the recipient, wherein steps (3) and (4) are carried out after steps (1) and (2).

In accordance with these embodiments, the maintaining of step (4) can be carried out, for example, by placing the sterile organ storage container, so sealed, within a well-insulated carton or shipping case at 2 to 8° C. In these examples, ice can be used to surround the sterile organ storage container, but ice should not be permitted to come in direct contact with the isolated lung.

Also in accordance with these embodiments, the isolated lung may be stored, based on its initial quality for, 1 to 12 hours, 3 to 12 hours, 6 to 12 hours, 9 to 12 hours, 10 to 12 hours, or 11 to 12 hours, prior to transplantation of the isolated lung into the recipient. Also in accordance with these embodiments, while the isolated lung is being so stored, the isolated lung may be transported to the recipient, e.g. transported within a medical care facility, such as a hospital and/or an organ transplantation centre, or between medical care facilities.

Also in some embodiments, the flushing volume of the solution is obtained from one or more sterile containers in which the solution has been stored. The one or more sterile containers can be sterile containers as discussed above, e.g. one or more 1000 mL sterile bags and/or one or more 3000 mL sterile bags, among others. In accordance with these embodiments, the flushing volume of the solution is not supplemented with additional ingredients before or during step (1).

Also in some embodiments, the filling volume of the solution is obtained from one or more sterile containers in which the solution has been stored. The one or more sterile containers can be sterile containers as discussed above, e.g. one or more 1000 mL sterile bags and/or one or more 3000 mL sterile bags, among others. In accordance with these embodiments, the filling volume of the solution is not supplemented with additional ingredients before or during step (2).

Also in some embodiments the organ preservation and/or perfusion solution is not supplemented with additional ingredients before or during any steps of the method. As will be appreciated, in accordance with these embodiments, the solution has been provided ready-to-use. As also will be appreciated, though, in other embodiments some volumes of the solution may be supplemented with additional ingredients, depending on circumstances of the flushing, storage, and/or transportation.

Example 1

Four test solutions were prepared according to Table 1.

TABLE 1

| Component | LPD | LPD + TRIS | LPD + CaCl2 | LPD + TRIS + CaCl2 |
|---|---|---|---|---|
| Dextran-40 | 50 g | 50 g | 50 g | 50 g |
| Sodium Chloride | 8 g | 8 g | 8 g | 8 g |
| D-Glucose monohydrate | 1 g | 1 g | 1 g | 1 g |
| Potassium Chloride | 400 mg | 400 mg | 400 mg | 400 mg |
| Magnesium sulphate 7H$_2$O | 200 mg | 200 mg | 200 mg | 200 mg |
| Disodium phosphate 12H$_2$O | 117 mg | 117 mg | 117 mg | 117 mg |
| Potassium dihydrogen phosphate | 63 mg | 63 mg | 63 mg | 63 mg |
| TRIS | not applicable | 74 mg | not applicable | 74 mg |
| Calcium Chloride 2H$_2$O | not applicable | not applicable | 242 mg | 242 mg |
| Water (Water for Injection) | add to 1 L | add to 1 L | add to 1 L | add to 1 L |
| pH adjusted to | Not applicable | 7.4 +/− 0.2 | Not applicable | 7.4 +/− 0.2 |

All four solutions were autoclaved simultaneously at 121° C. for 20 min, corresponding to an F0 of 15.

The glucose degradation in each solution post heat sterilization was measured using HPLC DRI glucose analysis according to the US Pharmacopeia for Dextran 40 in glucose injection. The results are summarised in Table 2.

TABLE 2

| Solution | % Glucose Degradation |
|---|---|
| LPD | 12.84 |
| LPD + CaCl2 | 12.64 |
| LPD + TRIS | 9.8 |
| LPD + TRIS + CaCl2 | 8.75 |

Calcium ions on their own did not provide a glucose stabilizing effect as pre-buffering did. However, the combination of calcium ions and pre-buffering provided a synergistic glucose stabilizing effect.

The formation of precipitate was also measured in two solutions. Table 3 summarizes turbidimetric data, after 24 months storage at two different temperatures, of LPD and LPD+calcium+TRIS. The measurement of turbidity was carried out using a method from the European Pharmacopeia, 2.2.1 Clarity and Degree of Opalescence of Liquids, with turbidity expressed as nephelometric turbidity units (hereinafter NTU).

TABLE 3

| 24 months | Turbidity PhEur 2.2.1 (storage at 5° C.) | Turbidity PhEur 2.2.1 (storage at 25° C.) |
|---|---|---|
| LPD | 1.84 NTU | 1.76 NTU |
| LPD + 3 mM TRIS + 0.5 mM Ca2+ | 1.61 NTU | 1.60 NTU |

REFERENCES

1. Heat sterilization of fluids for peritoneal dialysis gives rise to aldehydes. Nilsson-Thorell C B I, Muscalu N, Andrén A H, Kjellstrand P T, Wieslander A P. Perit Dial Int. 1993; 13(3):208-13.
2. Heat sterilization of glucose-containing fluids for peritoneal dialysis: biological consequences of chemical alterations. Wieslander A P, Kjellstrand P T, Rippel B. Perit Dial Int. 1995; 15(7 Suppl):S52-9; discussion S59-60
3. Can we prevent the degradation of glucose in peritoneal dialysis solutions? Ledebo I, Wieslander A, Kjellstrand P. Perit Dial Int. 2000; 20 Suppl 2:S48-51.
4. Importance of calcium in long-term preservation of the vasculature. Ingemansson R, Sjoberg T, Steen S. Ann Thorac Surg. 1996 April; 61(4):1158-62.

The invention claimed is:

1. A method of preparing an organ preservation and/or perfusion solution for an isolated tissue or organ in a sterile container, the organ preservation and/or perfusion solution having a pH of 6.6 to 7.8 at 25° C. following heat sterilization, the method comprising steps of:
   (1) preparing an initial solution comprising dextran, glucose at 0.5 to 5 g/L, calcium ions at 0.3 to 1.5 mM, and tris(hydroxymethyl)aminomethane (TRIS) buffer at 1 to 15 mM in water;
   (2) if the pH of the initial solution at 25° C. is not 7.0 to 7.8, then adjusting the pH of the initial solution to 7.0 to 7.8 at 25° C.; and (3) subjecting the initial solution having a pH of 7.0 to 7.8 at 25° C. to heat sterilization at 115 to 130° C. for at least 5 minutes to achieve an F0 of at least 10, wherein the initial solution is in a container during the heat sterilization, thereby obtaining the organ preservation and/or perfusion solution in the sterile container.

2. The method according to claim 1, wherein the initial solution comprises the dextran at 40 to 60 g/L.

3. The method according to claim 1, wherein the dextran has a weight average molecular weight (Mw) of 20000 to 70000 daltons.

4. The method according to claim 1, wherein the dextran comprises Dextran 40.

5. The method according to claim 1, wherein the initial solution comprises the glucose at 0.6 to 3 g/L.

6. The method according to claim 1, wherein the initial solution comprises the glucose at 0.8 to 2 g/L.

7. The method according to claim 1, wherein the initial solution comprises the TRIS buffer at 2 to 5 mM.

8. The method according to claim 1, where the water comprises water for injection.

9. The method according to claim 1, wherein the initial solution further comprises phosphate ions at 0.2 to 0.8 mM.

10. The method according to claim 1, wherein the organ preservation and/or perfusion solution does not include bicarbonate.

11. The method according to claim 1, wherein the heat sterilization is conducted at 118 to 123° C. for at least 10 minutes.

12. The method according to claim 1, wherein the initial solution does not exhibit formation of measurable precipitate during the heat sterilization.

13. The method according to claim 1, wherein glucose degradation during heat sterilization is less than 10%.

14. The method according to claim 1, wherein the sterile container comprises a sterile fluid bag.

15. A method of preparing an organ preservation and/or perfusion solution for an isolated tissue or organ in a sterile container, the organ preservation and/or perfusion solution having a pH of 6.9 to 7.6 at 25° C. following heat sterilization, the method comprising steps of:

(1) preparing an initial solution comprising dextran at 40 to 60 g/L, glucose at 0.5 to 5 g/L, calcium ions at 0.4 to 1 mM, tris(hydroxymethyl)aminomethane (TRIS) buffer at 2 to 5 mM, and phosphate in water;

(2) if the pH of the initial solution at 25° C. is not 7.2 to 7.6, then adjusting the pH of the initial solution to 7.2 to 7.6 at 25° C.; and (3) subjecting the initial solution having a pH of 7.2 to 7.6 at 25° C. to heat sterilization at 118 to 123° C. for at least 10 minutes to achieve an F0 of at least 10, wherein the initial solution is in a container during the heat sterilization, thereby obtaining the organ preservation and/or perfusion solution in the sterile container.

* * * * *